US009024090B2

(12) United States Patent
Zhang et al.

(10) Patent No.: US 9,024,090 B2
(45) Date of Patent: May 5, 2015

(54) CATALYSTS AND PROCESSES FOR PRODUCING BUTANOL

(71) Applicant: Celanese International Corporation, Irving, TX (US)

(72) Inventors: Cheng Zhang, Houston, TX (US); Kenneth Balliet, Pasadena, TX (US); Victor J. Johnston, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/719,870

(22) Filed: Dec. 19, 2012

(65) Prior Publication Data
US 2014/0171695 A1    Jun. 19, 2014

(51) Int. Cl.
| | |
|---|---|
| *C07C 27/00* | (2006.01) |
| *C07C 29/00* | (2006.01) |
| *B01J 29/00* | (2006.01) |
| *B01J 29/04* | (2006.01) |
| *B01J 29/06* | (2006.01) |
| *B01J 20/00* | (2006.01) |
| *B01J 21/00* | (2006.01) |
| *B01J 21/04* | (2006.01) |
| *B01J 23/00* | (2006.01) |
| *B01J 23/02* | (2006.01) |
| *B01J 23/04* | (2006.01) |
| *B01J 23/06* | (2006.01) |
| *B01J 23/08* | (2006.01) |
| *B01J 23/40* | (2006.01) |
| *B01J 23/42* | (2006.01) |
| *B01J 23/44* | (2006.01) |
| *B01J 23/56* | (2006.01) |
| *B01J 23/58* | (2006.01) |
| *B01J 23/60* | (2006.01) |
| *B01J 23/70* | (2006.01) |
| *B01J 23/72* | (2006.01) |
| *B01J 23/74* | (2006.01) |
| *B01J 23/78* | (2006.01) |
| *B01J 23/835* | (2006.01) |
| *C07C 29/34* | (2006.01) |
| *B01J 37/02* | (2006.01) |
| *B01J 23/62* | (2006.01) |
| *C07C 31/12* | (2006.01) |
| *B01J 37/08* | (2006.01) |
| *B01J 21/06* | (2006.01) |

(52) U.S. Cl.
CPC ............... *B01J 23/78* (2013.01); *B01J 23/835* (2013.01); *C07C 29/34* (2013.01); *B01J 37/0244* (2013.01); *B01J 37/08* (2013.01); *B01J 21/04* (2013.01); *B01J 21/066* (2013.01); *B01J 23/58* (2013.01); *B01J 23/624* (2013.01); *C07C 31/12* (2013.01); *C07C 29/00* (2013.01)

(58) Field of Classification Search
CPC .......... B01J 21/00; B01J 21/04; B01J 21/063; B01J 21/066; B01J 21/10; B01J 23/06; B01J 23/14; B01J 23/40; B01J 23/42; B01J 23/44; B01J 23/58; B01J 23/60; B01J 23/70; B01J 23/72; B01J 23/74; B01J 23/745; B01J 23/75; B01J 23/755; B01J 23/78; B01J 23/80; B01J 23/89; B01J 23/8946; B01J 23/8953; B01J 23/8966; B01J 29/0316; B01J 29/0352; B01J 29/042; B01J 29/064
USPC ......... 502/66, 73, 74, 87, 326–346, 349–351, 502/355, 415, 439
See application file for complete search history.

(56) References Cited

U.S. PATENT DOCUMENTS

| | | | |
|---|---|---|---|
| 2,762,847 A | 9/1956 | Miller et al. | |
| 3,200,063 A * | 8/1965 | Wilson | 208/111.15 |
| 3,864,407 A | 2/1975 | Yates | |
| 3,972,952 A | 8/1976 | Clark | |
| 4,011,273 A | 3/1977 | Abend et al. | |
| 4,229,374 A | 10/1980 | Slaugh et al. | |
| 4,533,775 A | 8/1985 | Fox et al. | |
| 4,551,444 A | 11/1985 | Lin et al. | |
| 4,687,877 A | 8/1987 | Bartley et al. | |
| 4,789,502 A * | 12/1988 | Slaugh | 554/143 |
| 4,943,551 A | 7/1990 | Dombek | |
| 5,095,156 A | 3/1992 | Radlowski et al. | |
| 5,159,125 A | 10/1992 | Hagen | |
| 5,300,695 A | 4/1994 | Radlowski | |
| 5,849,662 A * | 12/1998 | Praserthdam | 502/330 |
| 5,916,840 A * | 6/1999 | Ebner et al. | 502/331 |

(Continued)

FOREIGN PATENT DOCUMENTS

| | | |
|---|---|---|
| CN | 1528727 | 9/2004 |
| CN | 101530802 | 9/2009 |

(Continued)

OTHER PUBLICATIONS

OXO Alcohols, Process Economics Program Report 21E, Sep. 2010 (203 pages).
Matsu-ura, et al., Journal of Organic Chemistry, vol. 71, No. 21, pp. 8306-8308.
Dvornikoff, et al., Journal of Organic Chemistry, 1957, 11, pp. 540-542.
Carlini, et al., Journal of Molecular Catalysis A: Chemical, vol. 212, 2004, pp. 65-70.
DiCosimo, et al., Journal of Catalysis, vol. 190, 2000, pp. 261-275.
Office Action for U.S. Appl. No. 13/719,886 dated Feb. 6, 2014.
International Search Report and Written Opinion for PCT/US2013/076035 mailed May 13, 2014.

*Primary Examiner* — Cam N. Nguyen

(57) ABSTRACT

A catalyst composition for converting ethanol to higher alcohols, such as butanol, is disclosed. The catalyst composition comprises at least one alkali metal, at least a second metal and a support. The second metal is selected from the group consisting of palladium, platinum, copper, nickel, and cobalt. The support is selected from the group consisting of $Al_2O_3$, $ZrO_2$, MgO, $TiO_2$, zeolite, ZnO, and a mixture thereof.

20 Claims, No Drawings

(56) References Cited

U.S. PATENT DOCUMENTS

| | | | |
|---|---|---|---|
| 6,166,265 | A | 12/2000 | Kanand et al. |
| 6,218,326 | B1 | 4/2001 | Datta et al. |
| 6,323,383 | B1 | 11/2001 | Tsuchida et al. |
| 7,700,810 | B2 | 4/2010 | Kourtakis et al. |
| 7,700,811 | B2 | 4/2010 | Kourtakis et al. |
| 7,700,812 | B2 | 4/2010 | Kourtakis et al. |
| 7,700,813 | B2 | 4/2010 | Kourtakis et al. |
| 7,705,192 | B2 | 4/2010 | Kourtakis et al. |
| 7,807,857 | B2 | 10/2010 | Kourtakis et al. |
| 7,915,196 | B2 * | 3/2011 | Parent et al. .................. 502/335 |
| 8,071,822 | B2 | 12/2011 | Ozer et al. |
| 8,071,823 | B2 | 12/2011 | Ozer et al. |
| 8,232,433 | B2 | 7/2012 | Onda et al. |
| 8,569,203 | B2 * | 10/2013 | Weiner et al. ................. 502/349 |
| 8,778,833 | B2 * | 7/2014 | Madon et al. .................. 502/342 |
| 2002/0007097 | A1 | 1/2002 | Walsdorff et al. |
| 2007/0255079 | A1 | 11/2007 | Tsuchida et al. |
| 2009/0056204 | A1 | 3/2009 | Tsuchida et al. |
| 2010/0160692 | A1 | 6/2010 | Kourtakis et al. |
| 2010/0185021 | A1 | 7/2010 | Ross et al. |
| 2010/0205857 | A1 | 8/2010 | Dijk et al. |
| 2010/0298613 | A1 | 11/2010 | Tanaka et al. |
| 2011/0257443 | A1 * | 10/2011 | Weiner et al. ................. 568/885 |
| 2011/0288344 | A1 | 11/2011 | Grady et al. |
| 2012/0040427 | A1 | 2/2012 | Bell et al. |
| 2013/0131399 | A1 * | 5/2013 | Weiner et al. ................. 568/885 |
| 2013/0165700 | A1 * | 6/2013 | Zhou et al. .................... 568/885 |
| 2013/0165701 | A1 * | 6/2013 | Zhou et al. .................... 568/885 |
| 2013/0165703 | A1 * | 6/2013 | Weiner et al. ................. 568/885 |
| 2013/0178662 | A1 * | 7/2013 | Zhou et al. .................... 568/885 |
| 2013/0178666 | A1 * | 7/2013 | Zhou et al. .................... 568/885 |
| 2013/0178668 | A1 * | 7/2013 | Zhou et al. .................... 568/885 |
| 2013/0178669 | A1 * | 7/2013 | Zhou et al. .................... 568/885 |
| 2013/0184502 | A1 * | 7/2013 | Zhou et al. .................... 568/885 |
| 2013/0211150 | A1 * | 8/2013 | Zhou et al. .................... 568/885 |
| 2013/0225878 | A1 * | 8/2013 | Weiner et al. ................. 568/885 |
| 2013/0245332 | A1 * | 9/2013 | Weiner et al. ................. 568/885 |

FOREIGN PATENT DOCUMENTS

| | | |
|---|---|---|
| EP | 1050339 A1 | 11/2000 |
| GB | 814003 A | 5/1959 |
| GB | 2006773 A | 5/1979 |
| WO | WO 2006/059729 | 6/2006 |
| WO | WO 2009/097310 | 8/2009 |
| WO | WO 2009/097312 | 9/2009 |

* cited by examiner

CATALYSTS AND PROCESSES FOR PRODUCING BUTANOL

FIELD OF THE INVENTION

The present invention relates generally to a process of making higher molecular weight alcohols from ethanol and, in particular, to a catalytic conversion of ethanol to butanol.

BACKGROUND OF THE INVENTION

Studies have been done for economically viable processes to produce butanol. Like ethanol, butanol may be a possible solution to dependency on oil as both may be used as a fuel in an internal combustion engine. In fact, due to the longer hydrocarbon chain and non-polar characteristics, butanol may be a better fuel option than ethanol because butanol is more similar to gasoline than ethanol. In addition, butanol may be used in the manufacture of pharmaceuticals, polymers, pyroxylin plastics, herbicide esters and butyl xanthate. Butanol may also be used as a solvent for the extraction of essential oils or as an ingredient in perfumes; as an extractant in the manufacture of antibiotics, hormones, and vitamins; as a solvent for paints, coatings, natural resins, gums, synthetic resins, alkaloids, and camphor. Other applications of butanol includes as swelling agent in textiles; as a component of break fluids, cleaning formulations, degreasers, and repellents; and as a component of ore floatation agents and of wood-treating systems.

Butanol is typically produced industrially from petrochemical feedstock propylene in the presence of a rhodium-based homogeneous catalyst. During this process, propylene is hydroformylated to butyraldehyde and butyraldehyde is then hydrogenated to product butanol. However, due to the fluctuating natural gas and crude oil prices the cost of producing butanol using this method also becomes more unpredictable and significant.

It is known that butanol may be prepared by condensation from ethanol over basic catalyst at high temperature using the Guerbet reaction. The reaction mechanism for the conversion of ethanol to butanol via the Guerbet reaction comprises a four-step sequence as shown in reaction scheme 1. In the first step, ethanol is oxidized to intermediate aldehyde and two of the intermediate aldehydes undergo an aldol condensation reaction to form crotonaldehyde, which is reduced to butanol via hydrogenation. See, for example, J. Logsdon in *Kirk-othmer Encyclopedia of Chemical Technology*, John Wiley and Sons, Inc., New York, 2001; *J. Mol. Catal. A: Chem.*, 2004, 212, p. 65; and *J. Org. Chem.*, 2006, 71, p. 8306.

Various catalysts have been studied to improve the conversion and selectivity of ethanol to butanol. For example, M. N. Dvornikoff and M. W. Farrar, J. of Organic Chemistry (1957), 11, 540-542, discloses the use of a $MgO-K_2CO_3-CuCrO_2$ catalyst system to promote ethanol condensation to higher alcohols, including butanol. U.S. Pat. No. 5,300,695 discloses processes where an L-type zeolite catalyst, such as a potassium L-type zeolite, is used to react with an alcohol having X carbon atoms to produce alcohol with higher molecular weight.

The use of hydroxyapatite $Ca_{10}(PO_4)_6(OH)_2$, tricalcium phosphate $Ca_3(PO_4)_2$, calcium monohydrogen phosphate $CaHPO_4 \cdot (0-2)H_2O$, calcium diphosphate $Ca_2P_2O_7$, octacalcium phosphate $Ca_8H_2(PO_4)_6 \cdot 5H_2O$, tetracalcium phosphate $Ca_4(PO_4)_2O$, or amorphous calcium phosphate $Ca_3(PO_4)_2 \cdot nH_2O$, to convert ethanol to higher molecular weight alcohols are disclosed in WO2006059729.

Carlini et al., Journal of Molecular Catalysis A: Chemical (2005), 232, 13-20, discloses bifunctional heterogeneous hydrotalcites for converting methanol and n-propanol to isobutyl alcohol.

Others catalyst systems for making higher molecular weight alcohols from methanol or ethanol have also been studied. For example, U.S. Pat. No. 4,551,444 discusses the use of multi-component catalyst system using various metals; U.S. Pat. Nos. 5,095,156 and 5,159,125 discuss the impact of magnesium oxide; U.S. Pat. No. 4,011,273 discusses the use of insoluble lead catalysts; U.S. Pat. No. 7,807,857 focuses on Group II metal salts; and U.S. Pat. No. 4,533,775 discusses a catalyst system comprising a metal acetylide, a hydride, an alkoxide and promoter.

The references mentioned above are hereby incorporated by reference.

Nonetheless, the need remains for improved catalysts for making butanol from ethanol, especially those having improved activity and selectivity to butanol.

SUMMARY OF THE INVENTION

In a first embodiment, the present invention is directed to a catalyst composition for converting alcohols to higher alcohols. The catalyst composition comprises at least one alkali metal, at least one metal, and a support. The at least one alkali metal may be selected from the group consisting of lithium, sodium, potassium, rubidium, cesium, and francium. In addition, the at least a second metal may be selected from the group consisting of palladium, platinum, copper, nickel, and cobalt. Preferably, the support may be selected from the group consisting of $Al_2O_3$, $ZrO_2$, MgO, $TiO_2$, zeolite, ZnO, and a mixture thereof.

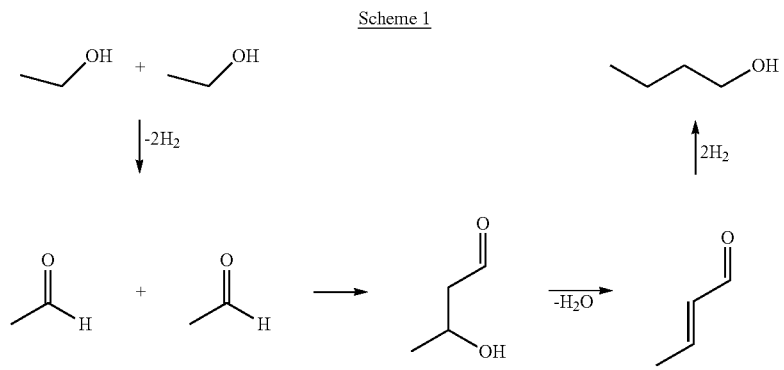

Scheme 1

In a second embodiment, the present invention is directed to a catalyst for converting alcohols to higher alcohols. The catalyst comprises a support, a first layer and a second layer on the support. Preferably, the support is selected from the group consisting of $Al_2O_3$, $ZrO_2$, MgO, $TiO_2$, zeolite, ZnO, and a mixture thereof. Preferably, the first layer comprises at least one alkali metal selected from the group consisting of lithium, sodium, potassium, rubidium, cesium, and francium. Preferably, the second layer comprising at least a second metal selected from the group consisting of palladium, platinum, copper, nickel, and cobalt.

In a third embodiment, the present invention is directed to a process for producing butanol. The process comprises the steps of feeding a gaseous stream comprising ethanol over a catalyst in a reactor to form butanol. Preferably, the catalyst comprises at least one alkali metal, at least one metal and a support. Preferably, the at least one alkali metal selected from the group consisting of lithium, sodium, potassium, rubidium, cesium, and francium. Preferably, the at least a second metal selected from the group consisting of palladium, platinum, copper, nickel, and cobalt. Preferably, the support is selected from the group consisting of $Al_2O_3$, $ZrO_2$, MgO, $TiO_2$, zeolite, ZnO, and a mixture thereof.

DETAILED DESCRIPTION OF THE INVENTION

Introduction

The present invention generally relates to a process for synthesizing a linear multi-carbon alcohol from an alcohol having two or fewer carbons that is useful as a chemical industry raw material and fuel composition or a mixture thereof.

Production of multi-carbon alcohols, like butanol, using most conventional processes has been limited by economic and environmental constraints. One of the best known processes is the Guerbet reaction. Specifically, ethanol may be used as the starting material to product butanol. However, intermediates of the reaction can form competing by-products and may lead to impurities in the butanol product. For example, diethyl ether and ethylene may be formed due to the dehydration of ethanol in the presence of an acidic catalyst. 1-hexanol may also be formed via the addition of aldehyde to butyraldehyde, a crotonaldehyde intermediate. Butyraldehyde may also react with other intermediates to form 2-ethylbutanol and 2-ethylhexanol. A crude mixture of the multi-carbon alcohol and impurities may increase the purification needed to recover butanol.

Catalysts, such as multi-catalyst systems, hydroxyapatite, and phosphate derivatives have been used to optimize the yields and selectivity to butanol. In addition, process conditions for the Guerbet reaction have also been studied to optimize the yields and selectivity to butanol.

The Guerbet reaction converts two moles of ethanol to one mole of butanol through multiple intermediates. The reaction comprising first oxidizing ethanol to form an aldehyde, condensing the aldehydes to 3-hydroxy-butyraldehyde, dehydrating the 3-hydroxy-butyraldehyde to crotonaldehyde, and reducing the crotonaldehyde to butanol.

It has now been discovered that certain catalysts effectively oxidizes ethanol to form an intermediate aldehyde, which forms crotonaldehyde, and reduces crotonaldehyde to butanol. Preferably, these catalysts serve as a base to oxidize ethanol and to promote aldol condensation, and also as a hydrogenating site for crotonaldehyde to form butanol. Surprisingly and unexpectedly, the inventors found that a catalyst system of at least one alkali metal and a metal coated on a support beneficially results in the improvement of ethanol conversion, and/or butanol selectivity. Preferably, the metal is selected from the group consisting of palladium, platinum, copper, nickel, and cobalt. Moreover, the novel catalyst system beneficially reduces the selectivities to DEE and ethylene. For purposes of this application, linear multi-carbon alcohols are preferred and thus butanol refers to n-butanol unless otherwise indicated.

Catalyst Composition

In one embodiment, the present invention is to a catalyst composition comprising at least one alkali metal or oxide thereof, at least a second metal or oxide thereof and a support. In one embodiment, the alkali metal is selected from the group consisting of lithium, sodium, potassium, rubidium, cesium, and francium. More preferably, the alkali metal is selected from the group consisting of lithium, potassium, and cesium. In one embodiment, the second metal is selected from the group consisting of palladium, platinum, copper, nickel, and cobalt. More preferably, the metal is selected from the group consisting of palladium and copper. It is understood that the alkali metal or metal may be present in its elementary form or as an oxide. Various combinations of the alkali metals and metals may be used to convert alcohols, such as ethanol, to higher alcohols, such as butanol. For example, metal combinations may include lithium/copper, lithium/palladium, potassium/copper, cesium/copper, or lithium/platinum.

In one embodiment, the catalyst comprises at least one alkali metal in an amount from 0.1 wt. % to 30 wt. %, e.g., from 0.5 wt. % to 20 wt. %, or from 1 wt. % to 16 wt. %. The catalyst may further comprise at least one metal in an amount from 0.01 wt. % to 20 wt. %, e.g., from 0.05 wt. % to 18 wt. %, or from 0.1 wt. % to 16 wt. %. Although not limited, in one embodiment, the catalyst may comprise more alkali metal than metal based on weight.

In one embodiment, the catalyst system further comprises an alkaline earth metal. The alkaline earth metal is selected from the group consisting of beryllium, magnesium, calcium, strontium, barium and radium. Optionally, the catalyst may comprise from 0.1 wt. % to 20 wt. % alkaline earth metal, e.g., from 0.5 wt. % to 18 wt. % or from 1 wt. % to 16 wt. %.

In one embodiment, the catalyst system further comprises a metalloid, such as germanium. Germanium may be used in combination with copper and/or potassium. The catalyst system may comprise from 0.1 wt. % to 20 wt. % germanium, e.g., from 0.5 wt. % to 18 wt. % or from 1 wt. % to 16 wt. %.

In one embodiment, the catalyst comprises a support that includes $Al_2O_3$, $ZrO_2$, MgO, $TiO_2$, zeolite, ZnO, and a mixture thereof. Preferably, the support comprises $Al_2O_3$, $ZrO_2$, or ZnO. Suitable supports may have a surface area that is at least 500 $m^2/g$, e.g., at least 200 $m^2/g$ or at least 50 $m^2/g$. These supports may be acidic supports that when used without an alkali metal and another metal would have a diethyl ether and/or ethylene selectivity that is greater than the butanol selectivity. Adding an alkali metal and metal in accordance with the present invention to the acidic supports favors butanol selectivity over diethyl ether and/or ethylene selectivity.

Alumina supports may include gamma-alumina ($\gamma$-$Al_2O_3$), etu-alumina ($\eta$-$Al_2O_3$), kappa alumina ($\kappa$-$Al_2O_3$), theta-alumina ($\theta$-$Al_2O_3$), or other alumina phase which is stable at temperatures use for catalyst calcination and conversion of alcohols, such as ethanol, to other alcohols, such as butanol. Unless otherwise indicated, for purposes of the present invention gamma-alumina is preferred.

Zeolite as used in the present application generally refers to microporous, aluminosilicate minerals. Examples of suitable zeolites include, but not limited to, silicoaluminophosphate (SAPO-34), clinoptilolite, ZSM-5, X-zeolite, and Y-zeolite.

The amount of support may vary depending on the metal loadings and generally comprises the balance of the catalyst. In one embodiment, the catalyst comprises the support in an amount from 60 wt. % to 99.89 wt. %, e.g., from 82 wt. % to 99.85 wt. %, or from 84 wt. % to 99.7 wt. %.

In one embodiment, the catalyst may comprise copper-lithium and γ-$Al_2O_3$. The catalyst composition may comprise from 0.1 wt. % to 20 wt. % copper, e.g., from 0.5 wt. % to 18 wt. %, or from 1 wt. % to 16 wt. %, and from 0.1 wt. % to 20 wt. % lithium, e.g., from 0.5 wt. % to 18 wt. %, or from 1 wt. % to 16 wt. %. The catalyst composition comprises from 60 wt. % to 98 wt. % γ-$Al_2O_3$, e.g., 64 wt. % to 99 wt. % or from 68 wt. % to 98 wt. %.

In another embodiment, the catalyst may comprise copper-potassium and γ-$Al_2O_3$. The catalyst composition may comprises from 0.1 wt. % to 20 wt. % copper, e.g., from 0.5 wt. % to 18 wt. %, or from 1 wt. % to 16 wt. %, and from 0.1 wt. % to 20 wt. % potassium, e.g., from 0.5 wt. % to 18 wt. %, or from 1 wt. % to 16 wt. %. The catalyst composition comprises from 60 wt. % to 99.8 wt. % γ-$Al_2O_3$, e.g., 64 wt. % to 99 wt. % or from 68 wt. % to 98 wt. %.

In yet another embodiment, the catalyst may comprise copper-potassium and $ZrO_2$. The catalyst composition may comprise from 0.1 wt. % to 20 wt. % copper, e.g., from 0.5 wt. % to 18 wt. %, or from 1 wt. % to 16 wt. % and from 0.1 wt. % to 20 wt. % potassium, e.g., from 0.5 wt. % to 18 wt. %, or from 1 wt. % to 16 wt. %. The catalyst composition comprises from 60 wt. % to 99.8 wt. % $ZrO_2$, e.g., 64 wt. % to 99 wt. % or from 68 wt. % to 98 wt. %.

In one embodiment, the catalyst may comprise copper-potassium-germanium and γ-$Al_2O_3$. In one embodiment, the catalyst composition comprises from 0.1 wt. % to 20 wt. % copper, e.g., from 0.5 wt. % to 18 wt. %, or from 1 wt. % to 16 wt. %, from 0.1 wt. % to 20 wt. % potassium, e.g., from 0.5 wt. % to 18 wt. %, or from 1 wt. % to 16 wt. %, and from 0.1 wt. % to 20 wt. % germanium, e.g., from 0.5 wt. % to 18 wt. %, or from 1 wt. % to 16 wt. %. The catalyst composition comprises from 60 wt. % to 99.8 wt. % γ-$Al_2O_3$, e.g., 64 wt. % to 99 wt. % or from 68 wt. % to 98 wt. %.

In one embodiment, the catalysts may comprise a support coated by two metal layers or three metal layers. In one embodiment, the one or more layers of metals are different metals. In one embodiment, the different layers of metals are coated on the support separately. In one embodiment, different metals may be mixed together prior to coating and coated on support together.

In another embodiment, the catalyst comprises a support, a first layer, second layer, and optionally a third layer. The first layer may be coated on the support. In one embodiment, the first layer is an alkali metal selected from the group consisting of lithium, sodium, potassium, rubidium, cesium, and francium. The second layer may be metal selected from the group consisting of palladium, platinum, copper, nickel, and cobalt. The second layer may partially coat the first layer and/or support. The second layer may be applied subsequent to the first layer, e.g. through a sequential multi-impregnation process. Each coating may comprise the alkali metal or metal in the weight amounts described above. In one embodiment, the catalyst may comprise an optional third layer or germanium. The third layer may partially coat the first/second layer and/or support. In another embodiment, the third layer may be coated between the first and the second layer, i.e., the third layer metal may be coated on the catalyst prior to the second layer metal. The optionally third layer may be applied subsequent to the first and second layer, e.g., through a sequential multi-impregnation process.

It has now been found that the metal-coated support catalysts of the present invention surprisingly achieve unexpectedly high butanol selectivity and yield in comparison to metal-free catalysts. Furthermore, the increase of butanol selectivity and yield is accompanied by the decrease of selectivity to by-products, such as diethyl ether (DEE) and ethylene. As stated above, DEE and ethylene are made in the reaction mixture by ethanol dehydration in the presence of an acid. In one embodiment, surprisingly and unexpectedly, it has now been found that the catalysts inhibit DEE and ethylene formation. For example, the butanol selectivity of at least 10%, e.g., at least 20%, or at least 30% may be achieved with the catalyst compositions. Surprisingly and unexpectedly, this increase of butanol selectivity is accompanied by the decrease of by-products selectivities. For example, selectivity to DEE is less than 10 wt. %, e.g., less than 5 wt. %, or less than 1 wt. %. Furthermore, the ethylene selectivity is less than 10 wt. %, e.g., less than 5 wt. %, or less than 1 wt. %. In one embodiment, diethyl ether and ethylene selectivity may be less than the butanol selectivity. Thus, the use of the catalyst favors the formation of butanol. Without being bound by theory, it is postulated as a result of coating the surface of the supports with at least one alkali metal and at least one metal, the catalyst composition may drive the Guerbet reaction favorably for butanol selectivity while suppressing the production of DEE and ethylene as compared to metal free support catalysts.

In one embodiment, surprisingly and unexpectedly, it has also been found that copper-potassium γ-$Al_2O_3$, copper-lithium γ-$Al_2O_3$, copper-potassium zirconium oxide, and copper-potassium-germanium γ-$Al_2O_3$ catalysts inhibit DEE and ethylene formation. Specifically, the inventors found that the catalyst compositions enhance the selectivity of butanol by suppressing the formation of DEE and ethylene.

Water is a byproduct when converting ethanol to butanol. Since water is more polar than ethanol, it is believed that water might compete with ethanol on the polar surface of the catalyst. The inventors have found that the surface polarity of the catalysts may be modified by introducing an organic metal precursor to the surface of the support to minimize the water/ethanol competition. The organic metal precursor may include pyridine, ammonium hydroxide tetramethylammonium hydroxide, tetrabutylammonium hydroxide, methyl amine, imidazole, and other suitable support modifiers. The organic metal precursors may be support modifiers that may adjust the chemical or physical properties of the support material such as the acidity or basicity of the support material. As such, the amount and residence time of ethanol on the surface of the catalyst may be increased and thereby promoting the carbon-carbon capillary condensation.

In other embodiments, in addition to a support, the catalyst may further comprise a support modifier. A modified support, in one embodiment, relates to a support that includes a support material and a support modifier, which, for example, may adjust the chemical or physical properties of the support material such as the acidity or basicity of the support material.

The catalyst may further comprise other additives, examples of which may include: molding assistants for enhancing moldability; reinforcements for enhancing the strength of the catalyst; pore-forming or pore modification agents for formation of appropriate pores in the catalyst, and binders. Examples of these other additives include oxalic acid, citric acid, polyacrylic acid, adipic acid, stearic acid, graphite, starch, cellulose, silica, alumina, glass fibers, silicon carbide, and silicon nitride. Preferably, these additives do not have detrimental effects on the catalytic performances, e.g., conversion and/or activity. These various additives may be added in such an amount that the physical strength of the catalyst does not readily deteriorate to such an extent that it becomes impossible to use the catalyst practically as an industrial catalyst.

In some embodiments, the catalyst composition comprises a pore modification agent, such as oxalic acid. A preferred type of pore modification agent is thermally stable and has a substantial vapor pressure at a temperature below 300° C., e.g., below 250° C. In one embodiment, the pore modification agent has a vapor pressure of at least 0.1 kPa, e.g., at least 0.5 kPa, at a temperature between 150° C. and 250° C., e.g., between 150° C. and 200° C.

The pore modification agent has a relatively high melting point, e.g., greater than 60° C., e.g., greater than 75° C., to prevent melting during the compression of the catalyst into a slug, tablet, or pellet. Preferably, the pore modification agent comprises a relatively pure material rather than a mixture. As such, lower melting components will not liquefy under compression during formation of slugs or tablets. For example, where the pore modification agent is a fatty acid, lower melting components of the fatty acid mixtures may be removed as liquids by pressing. If this phenomenon occurs during slug or tablet compression, the flow of liquid may disturb the pore structure and produce an undesirable distribution of pore volume as a function of pore diameter on the catalyst composition. In other embodiments, the pore modification agents have a significant vapor pressure at temperatures below their melting points, so that they can be removed by sublimination into a carrier gas.

Catalyst Preparation

The catalyst was synthesized using sequential impregnation method with a first metal coated as a first layer and a second metal coated on the first layer. A support is pressed under force for a predetermined time to form pellets. The pellets are lightly crushed to a desired particle size. An amount of the support in pellets form is measured and placed in a round bottom reactor. A first metal, preferably the alkali metal, is prepared by dissolving a metal precursor, such as a metal nitrate, in an amount of water and/or acetone to form a first metal precursor solution, which is impregnated on to the support by stepwise incipient wetness using the rotating dryer. The first metal coated support is dried in an oven at a desired temperature for a period of time and followed by calcination. The second metal layer is also prepared by dissolving a metal nitrate in water and/or acetone to form a second metal precursor solution. The second metal precursor solution is impregnated onto the first metal coated support by stepwise incipient wetness using the rotating dryer. The twice coated support is dried in the oven and calcinated at a desired temperature.

The initial temperature may range from 10° C. to 150° C., e.g., 30° C. to 120° C., or 50° C. to 90° C. The temperature ramping rate may be from 1° C. to 5° C. per minute. The final temperature may vary depending on the catalyst composition and generally ranges from 300° C. to 900° C., e.g., from 450° C. to 800° C., or from 500° C. to 700° C. The holding time is between 1 hour and 10 hours, e.g., between 2 hours and 8 hours, or between 4 hours and 6 hours. Depending on the metal used, other temperature profiles may be suitable. The calcination of the mixture may be done in an inert atmosphere, air or an oxygen-containing gas at the desired temperatures. Steam, a hydrocarbon or other gases or vapors may be added to the atmosphere during the calcination step or post-calcination to cause desired effects on physical and chemical surface properties as well as textural properties such as increase macroporosity.

As an example, the temperature profile may start at 60° C., increase at a rate of 5° C. per minute until the temperature reaches 600° C., and hold at 600° C. for 5 hours, and cooling to room temperature. For Group VIII metals, the calcination temperature may be lower, such as 300° C.

In one embodiment, the first metal precursor and the second metal precursor may be prepared separately or together and impregnated on to the support by stepwise incipient wetness using a rotating dryer. The support may have an evenly distributed first and second metal coated thereon. The coated support is dried in the oven and calcinated at a desired temperature.

In another embodiment, a multi-layered metal-coated support may be prepared by adding a third metal layer to the twice coated support. For example, the twice coated support may be cooled after calcination and a third metal nitrate or metal oxide may be coated thereon. The thrice-coated support may be dried and calcined.

In one embodiment, any suitable metal precursors may be used to make the catalyst composition. Non-limiting examples of suitable metal precursors include metal oxides, metal hydroxides (including hydrated oxides), metal salts of inorganic and organic acids such as, e.g., nitrates, nitrites, sulfates, halides (e.g., fluorides, chlorides, bromides and iodides), carbonates, phosphates, azides, borates (including fluoroborates, pyrazolylborates, etc.), sulfonates, carboxylates (such as, e.g., formates, acetates, propionates, oxalates and citrates), substituted carboxylates (including halogenocarboxylates such as, e.g., trifluoroacetates, hydroxycarboxylates, aminocarboxylates, etc.) and salts and acids wherein the metal is part of an anion (such as, e.g., hexachloroplatinates, tetrachloroaurate, tungstates and the corresponding acids).

Further non-limiting examples of suitable metal precursors for the processes of the present invention include alkoxides, complex compounds (e.g., complex salts) of metals such as, e.g., beta-diketonates (e.g., acetylacetonates), complexes with amines, N-heterocyclic compounds (e.g., pyrrole, aziridine, indole, piperidine, morpholine, pyridine, imidazole, piperazine, triazoles, and substituted derivatives thereof), aminoalcohols (e.g., ethanolamine, etc.), amino acids (e.g., glycine, etc.), amides (e.g., formamides, acetamides, etc.), and nitriles (e.g., acetonitrile, etc.). Non-limiting examples of preferred metal precursors include nitrates and oxides.

Non-limiting examples of specific metal precursors for use in the processes of the present invention include germanium oxide, germanium butoxide, germanium glycolate, germanium chloride, germanium acetate, germanium hydroxide, germanium methoxide, germanium nitride, and bis(2-carboxyethyl germanium sesquioxide); palladium bromide, palladium chloride, palladium iodide, palladium nitrate, palladium nitrate hydrate, tetraamine palladium nitrate, palladium oxide, palladium oxide hydrate, and palladium sulfate; copper oxide, copper hydroxide, copper nitrate, copper sulfate, copper chloride, copper formate, copper acetate, copper neodecanoate, copper ethylhexanoate, copper methacrylate, copper trifluoroacetate, copper acetoacetate and copper hexafluoroacetylacetonate; lithium nitrate, lithium acetate, lithium acetate dehydrate, and lithium phosphate; potassium nitrate, potassium acetate, potassium sulfate, and potassium sulfite; cobalt acetate, cobalt hydroxide, cobalt carbonate, cobalt nitrate, cobalt 2,4-pentaedionate, cobalt formate, cobalt oxide, cobalt chloride, cobalt alkoxide, cobalt perchlorate, and cobalt carboxylate; and cesium nitrate, cesium chloride, cesium hydroxide, cesium carbonate, cesium oxalate, cesium perchlorate, cesium propionate, and cesium formate. The above compounds may be employed as such or optionally in the form of solvates and the like such as, e.g., as hydrates. Examples of specific metal precursors that may be used in the present invention include germanium oxide, bis (2-carboxyethyl germanium sesquioxide), palladium nitrate hydrate, copper nitrate hydrate, potassium nitrate, cesium nitrate, lithium nitrate, and cobalt nitrate.

The use of mixtures of different compounds, e.g., different salts, of the same metal and/or the use of mixtures of compounds of different metals and/or of mixed metal precursors (e.g., mixed salts and/or mixed oxides) is also contemplated by the present invention. Accordingly, the term "metal precursor" as used herein includes both a single metal precursor and any mixture of two or more metal precursors. In a preferred embodiment, the catalyst composition is made using at least one alkali metal, metalloid or transition metal and a support. The catalyst composition may further comprise an alkaline earth metal.

Production of Butanol

Suitable reactions and/or separation scheme may be employed to form a crude product stream comprising butanol using the catalysts. For example, in some embodiments, the crude product stream is formed by contacting a low molecular weight alcohol, e.g., ethanol, with the catalysts to form the crude higher alcohol product stream, i.e., a stream with butanol. Preferably, the catalyst is a support coated by at least one alkali metal and metal. In a preferred embodiment, the crude product stream is the reaction product of the condensation reaction of ethanol, which is conducted over a metal-coated support. In one embodiment, the crude product stream is the product of a vapor phase reaction.

The feedstream may be a gaseous stream comprising ethanol. Preferably, the gaseous stream comprise more than 5 vol. % ethanol, e.g., more than 10 vol. % or more than 20 vol. %. The feedstream may also comprise other molecules such as pyridine, $NH_3$, and alkyl amine. Inert gases may be in the gaseous stream and thus may include nitrogen, helium, argon, and methane. Preferably, no hydrogen is introduced with the gaseous stream, and thus the gaseous stream is substantially free of hydrogen. Without being bound by theory, the hydrogen needed for the intermediate reactions may be produced in situ.

In some embodiments, the condensation reaction may achieve favorable conversion of ethanol and favorable selectivity and productivity to butanol. For purposes of the present invention, the term "conversion" refers to the amount of ethanol in the feed that is converted to a compound other than ethanol. Conversion is expressed as a percentage based on ethanol in the feed. The conversion of ethanol may be at least 20%, e.g., at least 30%, at least 40%, or at least 60%.

Selectivity, as it refers to the formation of butanol, is expressed as the ratio of the amount of carbon in the desired product(s) and the amount of carbon in the total products. Preferably, the selectivity to butanol is at least 30%, e.g., at least 40%, or at least 60%. In some embodiments, the catalyst selectivity to $C_{4+}$ alcohols, e.g., n-butanol, isobutanol, 2-butanol, tert-butanol, 1-hexanol, 2-ethylbutanol, or 2-ethylhexanol, is at least 30%, e.g., at least 50%, at least 60%, or at least 80%.

Preferred embodiments of the process demonstrate a low selectivity to undesirable products, such as diethyl ether and ethylene. The selectivity to these undesirable products preferably is less than 20%, e.g., less than 5% or less than 1%. More preferably, these undesirable products are not detectable.

The ethanol may be fed to the reactor as a liquid stream or a vapor stream. Preferably, the ethanol is fed as a vapor stream. The reactor may be any suitable reactor or combination of reactors. Preferably, the reactor comprises a fixed bed reactor or a series of fixed bed reactors. In one embodiment, the reactor is a gas flow catalytic reactor or a series of gas flow catalytic reactors. Of course, other reactors such as a continuous stirred tank reactor or a fluidized bed reactor may be employed. In one embodiment, the vapor ethanol stream is substantially free of hydrogen, e.g., less than 1 wt. % hydrogen, less than 0.1 wt. %, or less than 0.01 wt. %.

The condensation reaction may be conducted at a temperature of at least 200° C., e.g., at least 300° C., or at least 350° C. In terms of ranges, the reaction temperature may range from 200° C. to 500° C., e.g., from 250° C. to 400° C., or from 250° C. to 350° C. Reaction time may range from 0.01 to 100 hours, e.g., from 1 to 80 hours, or from 5 to 80 hours. Reaction pressure is not particularly limited, and the reaction is typically performed near atmospheric pressure. In one embodiment, the reaction may be conducted at a pressure ranging from 0.1 kPa to 9,000 kPa, e.g., from 20 kPa to 5,000 kPa, or from 90 to 3,500 kPa. The ethanol conversion may vary depending upon the reaction temperature and/or pressure.

In one embodiment, the reaction is conducted at a gas hourly space velocity ("GHSV") greater than 600 $hr^{-1}$, e.g., greater than 1,000 $hr^{-1}$ or greater than 2,000 $hr^{-1}$. The GHSV may range from 600 $hr^{-1}$ to 10,000 $hr^{-1}$, e.g., from 1,000 $hr^{-1}$ to 8,000 $hr^{-1}$ or from 1,500 $hr^{-1}$ to 7,500 $hr^{-1}$.

An inert or reactive gas may be supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors. The addition of these additional components may improve reaction efficiencies.

In one embodiment, the unreacted components such as the ethanol as well as the inert or reactive gases that remain are recycled to the reactor after sufficient separation from the desired product.

EXAMPLES

Example 1

3 wt. % Copper Lithium γ-Aluminum Oxide

The catalyst was synthesized using sequential impregnation method with lithium on the inner layer and copper on the outer layer. γ-Aluminum oxide was crushed to particle size of 0.85 mm and 1.18 mm. The lithium layer was prepared by measuring and placing 10 g of the crushed γ-aluminum oxide in a round bottom reactor. 0.34 g of lithium nitrate was dissolved in 5 g of water, followed by impregnating to the γ-aluminum oxide by stepwise incipient wetness using a rotating dryer. The lithium coated γ-aluminum oxide was dried in an oven at 120° C. for 5 hours, followed by calcination using the following temperature program: start at 60° C., ramp to 500° C. at 2° C./min, hold at 500° C. for 5 hours, followed by cooling to room temperature. The copper layer was prepared by dissolving 1.09 g of copper nitrate hydrate in 5 g of water, followed by impregnating to the lithium coated γ-aluminum oxide by stepwise incipient wetness using a rotating dryer. The copper-lithium coated γ-aluminum oxide was dried in an oven at 120° C. for 5 hours, followed by calcination using the following temperature program: start at 60° C., ramp to 350° C. at 2° C./min, hold at 350° C. for 5 hours, followed by cooling to room temperature.

Example 2

3 wt. % Copper Potassium γ-Aluminum Oxide

The catalyst was synthesized using sequential impregnation method with potassium on the inner layer and copper on the outer layer. The potassium layer was prepared by measuring and placing 10 g of the crushed γ-aluminum oxide (particle size of 0.85 mm and 1.18 mm) in a round bottom reactor. 0.82 g of potassium nitrate was dissolved in 5 g of water, followed by impregnating to the γ-aluminum oxide by stepwise incipient wetness using a rotating dryer. The potassium coated γ-aluminum oxide was dried in an oven at 120° C. for 5 hours, followed by calcination using the following temperature program: start at 60° C., ramp to 500° C. at 2° C./min, hold at 500° C. for 5 hours, followed by cooling to room temperature. The copper layer was prepared by dissolving 1.09 g of copper nitrate hydrate in 5 g of water, followed by impregnating to the potassium coated γ-aluminum oxide by stepwise incipient wetness using a rotating dryer. The copper-potassium coated γ-aluminum oxide was dried and calcined under the same conditions.

Example 3

3 wt. % Copper Potassium Zirconium Oxide

The catalyst was synthesized using sequential impregnation method with potassium on the inner layer and copper on the outer layer. The potassium layer was prepared by measuring and placing 10 g of the crushed zirconium oxide (0.85 mm and 1.18 mm) in a round bottom reactor. 0.82 g of potassium nitrate was dissolved in 5 g of water, followed by impregnating to the zirconium oxide by stepwise incipient wetness using a rotating dryer. The potassium coated zirconium oxide was dried and calcined as described in Example 2. The copper layer was prepared by dissolving 1.09 g of copper nitrate hydrate in 5 g of water, followed by impregnating to the potassium coated zirconium oxide by stepwise incipient wetness using a rotating dryer. The copper-potassium coated zirconium oxide was dried in an oven at 120° C. for 5 hours, followed by calcination using the following temperature program: start at 60° C., ramp to 350° C. at 2° C./min, hold at 350° C. for 5 hours, followed by cooling to room temperature.

Example 4

3 wt. % Copper Potassium Germanium γ-Aluminum Oxide

The catalyst was synthesized using sequential impregnation method with potassium on the inner layer, germanium on the medium layer, and copper on the outer layer. The potassium layer was prepared by measuring and placing 10 g of the crushed γ-aluminum oxide (0.85 mm and 1.18 mm) in a round bottom reactor. 0.82 g of potassium nitrate was dissolved in 5 g of water, followed by impregnating to the γ-aluminum oxide by stepwise incipient wetness using a rotating dryer. The potassium coated γ-aluminum oxide was dried and calcined as described in Example 2. The germanium layer was prepared by dissolving 0.49 g of bis(2-carboxyethyl germanium (IV) sesquioxide) in 25 g of distilled water and heating the mixture at about 65° C. until the solution was clear. The resulted clear solution was impregnated to the potassium coated γ-aluminum oxide by stepwise incipient wetness using a rotating dryer. The obtained sample was dried and calcined under the same conditions. The copper layer was prepared by dissolving 1.09 g of copper nitrate hydrate in 5 g of water, followed by impregnating to the potassium germanium coated γ-aluminum oxide by stepwise incipient wetness using a rotating dryer. The copper potassium germanium coated γ-aluminum oxide was dried and calcined under the same conditions.

Comparative Example A 3 wt. % Copper γ-Aluminum Oxide

The catalyst was synthesized using impregnation method. The catalyst was prepared by dissolving 1.09 g of copper nitrate hydrate in 5 g of water, followed by impregnating to the γ-aluminum oxide (0.85 mm and 1.18 mm) by stepwise incipient wetness using a rotating dryer. The copper coated γ-aluminum oxide was dried in an oven at 120° C. for 5 hours, followed by calcination using the following temperature program: start at 60° C., ramp to 500° C. at 2° C./min, hold at 500° C. for 5 hours, followed by cooling to room temperature.

Comparative Example B 3 wt. % Germanium γ-Aluminum Oxide

The catalyst was synthesized using impregnation method. γ-Aluminum oxide was crushed to particle size of 0.85 mm and 1.18 mm. The catalyst was prepared by dissolving 0.49 g of bis(2-carboxyethyl germanium (IV) sesquioxide) in 25 g of distilled water and heating the mixture at about 65° C. until the solution was clear. The resulted clear solution was impregnated to the γ-aluminum oxide by stepwise incipient wetness using a rotating dryer. The germanium coated γ-aluminum oxide was dried and calcined as described in Comparative Example A.

Comparative Example C 3 wt. % Potassium γ-Aluminum Oxide

The catalyst was synthesized using impregnation method. γ-Aluminum oxide was crushed to particle size of 0.85 mm and 1.18 mm. The catalyst was prepared by dissolving 0.82 g of potassium nitrate in 5 g of water, followed by impregnating to the γ-aluminum oxide by stepwise incipient wetness using a rotating dryer. The potassium coated γ-aluminum oxide was dried and calcined as described in Comparative Example A.

Example 5

Catalyst Evaluation

The above catalysts were prepared and evaluated. γ-Aluminum oxide, zirconium oxide without any metal coating were evaluated under the same testing conditions to serve as control. A fixed bed gas flow catalytic reactor was used as a reactor. 3 ml of the catalysts was filled in a stainless steel tube reactor with a diameter of 0.95 cm. As a pretreatment, hydrogen reduction was conducted for 1 hour under a carrier gas atmosphere (10% $H_2/N_2$ base; flow rate 125 ml/min) at 400° C. After the pretreatment, the testing was conducted at a temperature between 250° C. and 325° C. and pressure between 1 kPa and 5,100 kPa, nitrogen flow rate was at 125 sccm and ethanol flow rate was at 0.2 ml/min. The reaction duration ranges from 5 hours to 80 hours.

The ethanol conversion, butanol product selectivity, butanol yield, and $C_{4+}$ alcohol selectivity for γ-aluminum oxide catalyst and γ-aluminum oxide as reference is shown below in Tables 2-3.

TABLE 1

Testing condition: 400° C. and 3,400 kPa

| Catalysts | Ethanol Conversion (%) | Butanol Selectivity (%) | Yield (%) | C$_{4+}$ Alcohols Selectivity (%) | DEE Selectivity (%) | Ethylene Selectivity (%) |
|---|---|---|---|---|---|---|
| γ-Al$_2$O$_3$ | 93 | 0 | 0 | 0 | 1 | 65 |
| Example 1 | 57 | 70 | 40 | 84 | 8 | 0 |

As shown in Table 1, γ-aluminum oxide has an ethanol conversion of 93%, but has a 0% butanol selectivity and 65% ethylene selectivity. By coating γ-aluminum oxide with copper/lithium, the butanol selectivity, butanol yield, C$_{4+}$ alcohols selectivity increased significantly while the ethylene selectivity is suppressed.

TABLE 2

Testing condition: 290° C. and 3,400 kPa

| Catalysts | Ethanol Conversion (%) | Butanol Selectivity (%) | Yield (%) | C$_{4+}$ Alcohols Selectivity (%) | DEE Selectivity (%) | Ethylene Selectivity (%) |
|---|---|---|---|---|---|---|
| γ-Al$_2$O$_3$ | 61 | 0 | 0 | 0 | 96 | 7 |
| Example 2 | 60 | 40 | 24 | 54 | 0 | 0 |

As shown in Table 2, γ-aluminum oxide has an ethanol conversion of 61%, but has a 0% butanol selectivity and 96% DEE selectivity. By coating γ-aluminum oxide with copper/potassium, the butanol selectivity, butanol yield, C$_{4+}$ alcohols selectivity increased significantly while suppressing DEE and ethylene selectivity to 0 wt. %.

The ethanol conversion, butanol product selectivity, butanol yield, and C$_{4+}$ alcohol selectivity for γ-aluminum oxide catalysts are shown below in Table 3.

TABLE 3

Testing condition: 270° C. and 3,400 kPa

| Catalysts | Ethanol Conversion (%) | Butanol Selectivity (%) | Yield (%) | C$_{4+}$ Alcohols Selectivity (%) | DEE Selectivity (%) | Ethylene Selectivity (%) |
|---|---|---|---|---|---|---|
| γ-Al$_2$O$_3$ | 39 | 0 | 0 | 0 | 98 | 1 |
| Comp. A | 40 | 12 | 5 | 16 | 66 | 1 |
| Comp. B | 16 | 0 | 0 | 0 | 97 | 1 |
| Comp. C | 8 | 0 | 0 | 0 | 82 | 5 |
| Example 2 | 43 | 42 | 18 | 51 | 0 | 0 |
| Example 4 | 49 | 46 | 23 | 56 | 0 | 0 |

As shown in Table 3, single metal coated γ-Al$_2$O$_3$ catalysts, including copper coated γ-Al$_2$O$_3$(Comp. A), germanium coated γ-Al$_2$O$_3$(Comp. B), and potassium coated γ-Al$_2$O$_3$ (Comp. C) are compared with copper-potassium coated γ-Al$_2$O$_3$ (Example 2) and copper-potassium-germanium coated γ-Al$_2$O$_3$ (Example 4). Uncoated γ-Al$_2$O$_3$ was also examined. As shown, with the exception of Comp. A, coated and uncoated γ-Al$_2$O$_3$ do not show any butanol selectivity. In comparison, Example 2 and Example 4 increase ethanol conversion, butanol selectivity, butanol yield and C$_{4+}$ alcohols selectivity. Surprisingly and unexpectedly, the two and three metal coated γ-Al$_2$O$_3$ catalysts decrease DEE and ethylene selectivity to zero.

The ethanol conversion, butanol product selectivity, butanol yield, and C$_{4+}$ alcohol selectivity for zirconium oxide catalyst and zirconium oxide as reference are shown below in Table 4.

TABLE 4

Testing condition: 360° C. and 3,400 kPa

| Catalysts | Ethanol Conversion (%) | Butanol Selectivity (%) | Yield (%) | C$_{4+}$ Alcohols Selectivity (%) | DEE Selectivity (%) | Ethylene Selectivity (%) |
|---|---|---|---|---|---|---|
| ZrO$_2$ | 21 | 14 | 3 | 20 | 30 | 34 |
| Example 3 | 88 | 38 | 33 | 62 | 1 | 0 |

As shown in Table 4, the copper/potassium coated zirconium oxide has better ethanol conversion, butanol selectivity, butanol yield, $C_{4+}$ alcohols selectivity and lower DEE selectivity and ethyl selectivity than the metal free zirconium oxide and the one-metal coated zirconium oxide.

While the invention has been described in detail, modifications within the spirit and scope of the invention will be readily apparent to those of skill in the art. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the invention.

We claim:

1. A catalyst for converting alcohols to higher alcohols, the catalyst comprising:
   copper;
   at least one alkali metal selected from the group consisting of lithium, sodium, potassium, rubidium, cesium, and francium; and
   a support selected from the group consisting of $Al_2O_3$, $ZrO_2$, MgO, $TiO_2$, zeolite, ZnO, and a mixture thereof,
   wherein the support has an average particle size ranging from 0.85 mm to 1.18 mm.

2. The catalyst of claim 1, wherein the at least one alkali metal is selected from the group consisting of lithium, potassium, and cesium.

3. The catalyst of claim 1, wherein the at least one alkali metal is present in an amount from 0.1 wt. % to 30 wt. %.

4. The catalyst of claim 1, wherein the support is present in an amount from 60 wt. % to 99.99 wt. %.

5. The catalyst of claim 1, wherein the catalyst comprises one of the following combinations of metals:
   copper and lithium;
   copper and potassium; and
   copper, potassium and zirconium; and
   copper, potassium, and germanium.

6. The catalyst of claim 1, wherein the catalyst further comprises an alkaline earth metal selected from the group consisting of beryllium, magnesium, calcium, strontium, barium and radium.

7. The catalyst of claim 1, wherein the catalyst further comprises germanium.

8. A catalyst for converting alcohols to higher alcohols, the catalyst comprising:
   a support selected from the group consisting of $Al_2O_3$, $ZrO_2$, MgO, $TiO_2$, zeolite, ZnO, and a mixture thereof;
   a first layer comprising at least one alkali metal selected from the group consisting of lithium, sodium, potassium, rubidium, cesium, and francium; and
   a second layer comprising copper.

9. The catalyst of claim 8, wherein the catalysts comprise from 0.1 to 30 wt. % of the at least one alkali metal and from 0.01 to 20 wt. % copper.

10. The catalyst of claim 8, wherein the support has an average particle size ranging from 0.85 mm to 1.18 mm.

11. A process for producing butanol, the process comprising the steps of:
    feeding a gaseous stream comprising ethanol over a catalyst in a reactor to form butanol, wherein the catalyst comprises:
    at least one alkali metal selected from the group consisting of lithium, sodium, potassium, rubidium, cesium, and francium;
    copper; and
    a support selected from the group consisting of $Al_2O_3$, $ZrO_2$, MgO, $TiO_2$, zeolite, ZnO, and a mixture thereof,
    wherein the support has an average particle size ranging from 0.85 mm to 1.18 mm.

12. The process of claim 11, wherein the reactor is operated at a temperature from 200° C. to 500° C.

13. The process of claim 11, wherein the reactor is operated at a pressure from 100 kPa to 20,000 kPa.

14. The process of claim 11, wherein ethanol conversion is at least 20%.

15. The process of claim 11, wherein butanol selectivity is at least 30%.

16. The process of claim 11, wherein ethylene selectivity is less than 10%.

17. The process of claim 11, wherein diethyl ether selectivity is less than 10%.

18. The process of claim 11, wherein the at least one alkali metal is present in an amount from 0.1 wt. % to 20 wt. %, the at least second metal is present in an amount from 0.01 wt. % to 20 wt. %, and the support is present in an amount from 60 wt. % to 99.89 wt. %.

19. The process of claim 11, wherein the gaseous stream is substantially free of hydrogen.

20. A process for producing butanol, the process comprising the steps of:
    feeding a gaseous stream comprising ethanol over a catalyst in a reactor to form butanol, wherein the catalyst comprises:
    a support selected from the group consisting of $Al_2O_3$, $ZrO_2$, MgO, $TiO_2$, zeolite, ZnO, and a mixture thereof;
    a first layer comprising at least one alkali metal selected from the group consisting of lithium, sodium, potassium, rubidium, cesium, and francium; and
    a second layer comprising copper.

* * * * *